United States Patent [19]

Valosen

[11] Patent Number: 4,816,617
[45] Date of Patent: Mar. 28, 1989

[54] CABLE HANDLING SYSTEM

[75] Inventor: Charles J. Valosen, Mukwonago, Wis.

[73] Assignee: General Electric Company, Milwaukee, Wis.

[21] Appl. No.: 120,457

[22] Filed: Nov. 13, 1987

[51] Int. Cl.[4] .......................... H01B 7/04; H05G 1/06; H02G 11/00

[52] U.S. Cl. .................................... 174/86; 174/68.1; 174/97; 191/12 R; 378/194

[58] Field of Search .................. 174/68 R, 69, 86, 97; 378/194; 191/12 R; 439/6, 10, 21

[56] References Cited

U.S. PATENT DOCUMENTS

| | | | |
|---|---|---|---|
| 2,785,382 | 3/1957 | Lamb | 174/68 R |
| 3,038,558 | 6/1962 | Plummer | 174/DIG. 11 X |
| 3,120,411 | 2/1964 | Strumpbell | 174/69 |
| 3,127,469 | 3/1964 | Rather et al. | 174/69 |
| 3,163,707 | 12/1964 | Darling | 174/69 |
| 3,301,940 | 1/1967 | Rischard et al. | 174/86 |
| 3,340,900 | 9/1967 | Spurlock | 138/136 |
| 3,424,855 | 1/1969 | Sharkey et al. | 174/97 |
| 4,234,146 | 11/1980 | Shima et al. | 191/12 R X |
| 4,246,482 | 1/1981 | Zupancic | 378/194 X |
| 4,288,700 | 9/1981 | Grass et al. | 174/86 |
| 4,298,801 | 11/1981 | Heitman et al. | 250/447 |
| 4,311,293 | 1/1982 | Tenniswood | 248/49 |
| 4,365,343 | 12/1982 | Grady et al. | 378/181 |

FOREIGN PATENT DOCUMENTS 757357 9/1956 United Kingdom .................. 174/97

OTHER PUBLICATIONS

Product Data Sheet of Philips of Holland, "Poly Diagnost U/V", 9/18/87.

*Primary Examiner*—Morris H. Nimmo
*Attorney, Agent, or Firm*—Quarles & Brady

[57] ABSTRACT

A cable handling system for routing a group of cables to a rotatable hub having an arm extending therefrom has a sleeve which partitions the group of cables into side-by-side subgroups. The sleeve is flexible and allows the cables to slide and flex within it. Forward and rearward straps attach the sleeve to a forward position on the arm and a fixed rearward position to hold the sleeve longitudinally in place and subject it to longitudinal and transverse tension. A cable rotator holds the cables next to the hub where they enter the hub area and allows them to pivot in the plane of rotation of the hub as the hub is rotated but does not allow longitudinal sliding of the cables. In the arm area, rigid longitudinal partitions maintain the subgrouping of the cables and the cables are enclosed on the top and bottom to longitudinally support the cables against buckling and facilitate sliding among the cables.

13 Claims, 6 Drawing Sheets

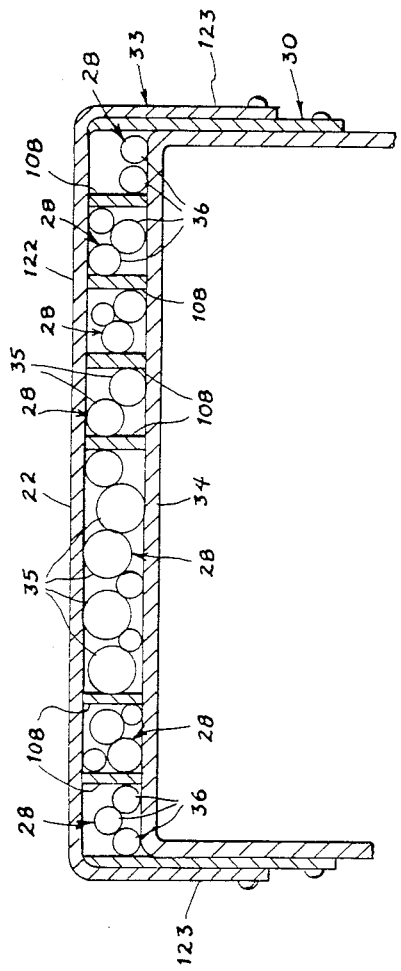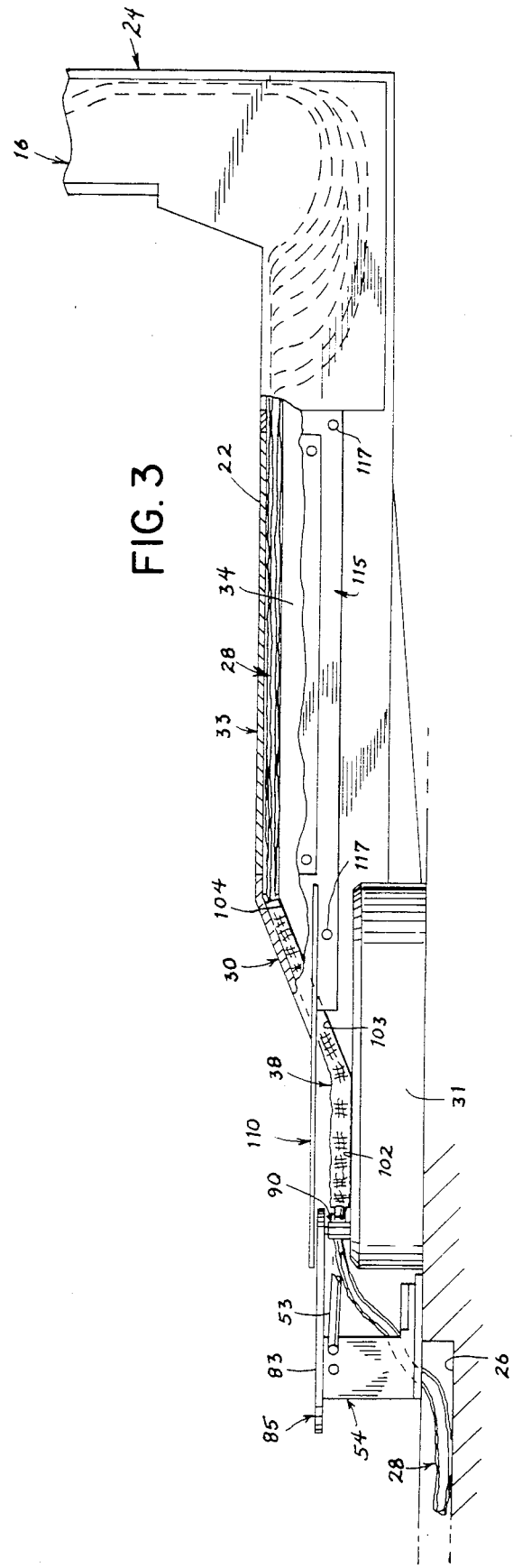

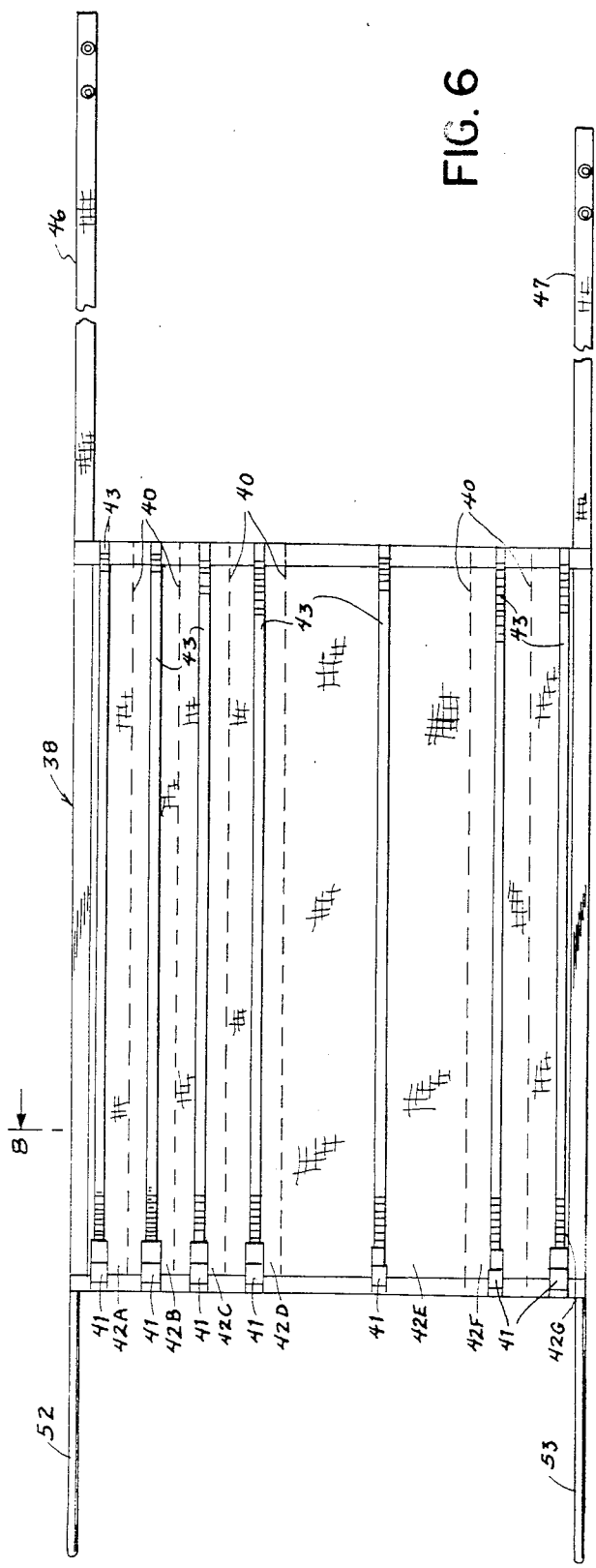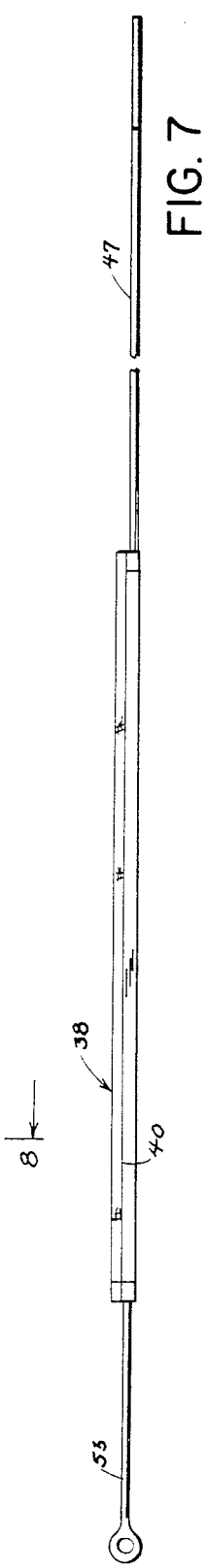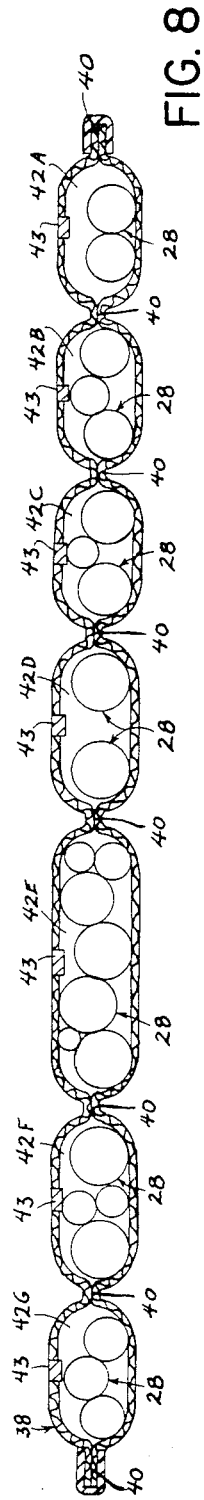

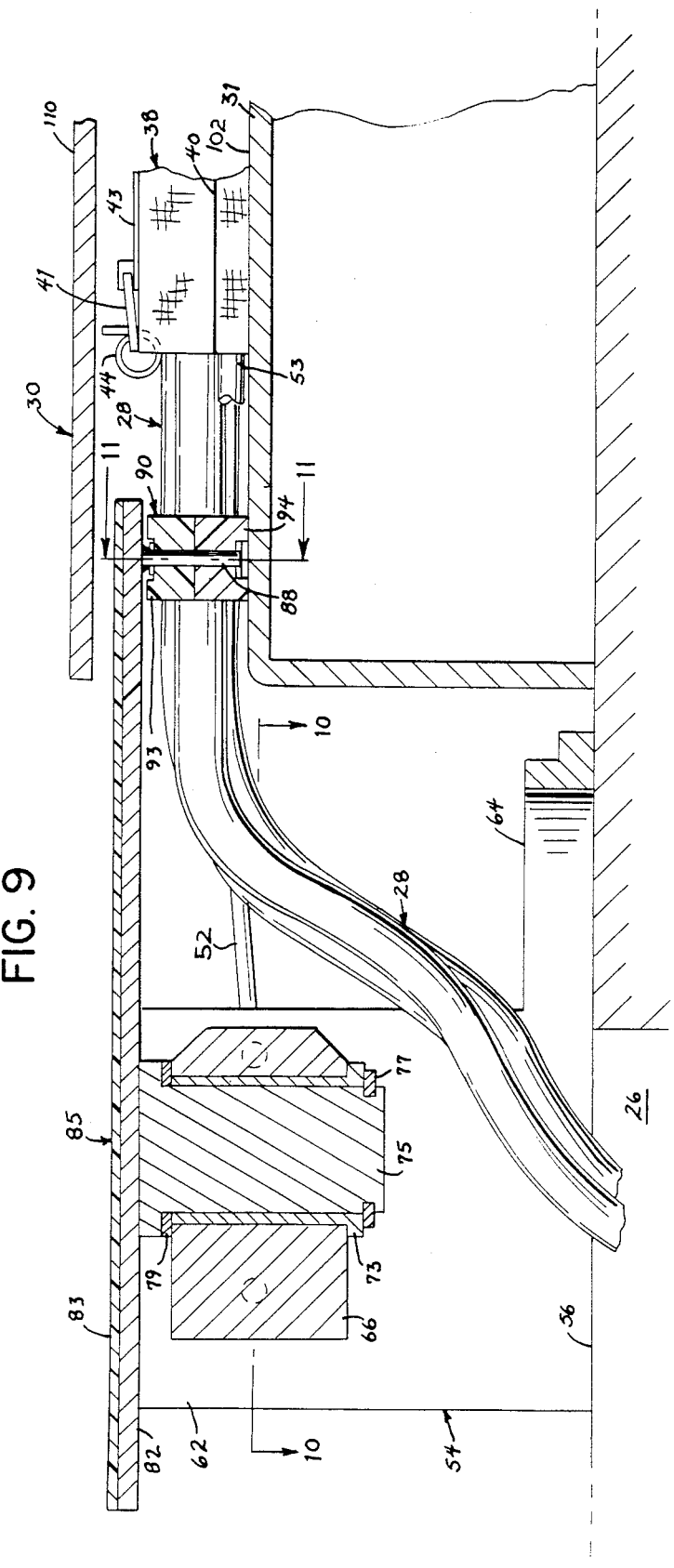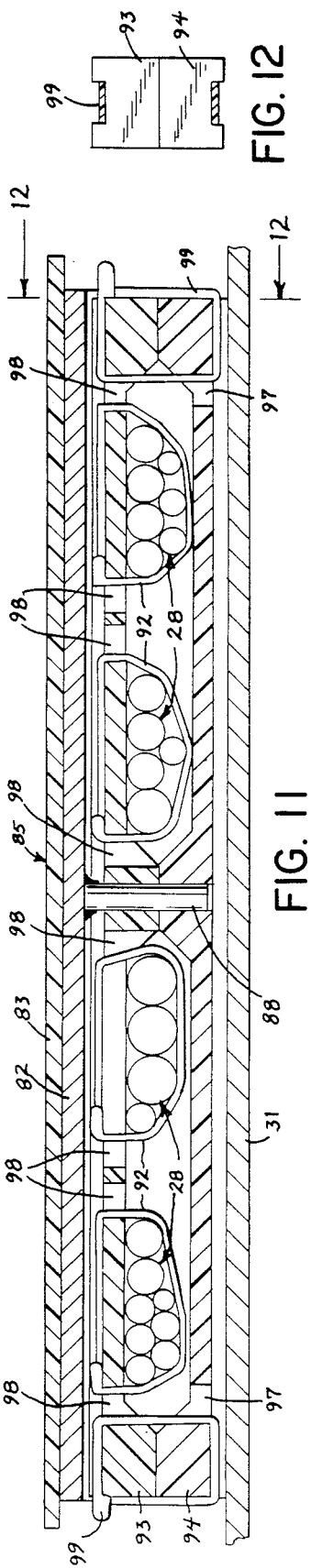

CABLE HANDLING SYSTEM

BACKGROUND OF THE INVENTION

1. Field Of The Invention

This invention relates to a system for routing cables from a stationary location to a moveable location, and specifically to a system for routing cables to a rotatable hub and to an arm extending from the hub.

2. Discussion Of The Prior Art

It is often necessary to route cables (e.g. electrical, fiber optic, protective sheathing, etc.) from a stationary location to a location which is pivotable about one or more axes. Because there is motion between the stationary origin of the cables and their destination, they must be able to undergo movement and flexing as the destination is moved.

One approach for routing cables to a pivotable location which has been tried is to suspend the cables from a remote location and provide slack in them to accommodate the range of motion and allow for flexing. For example, for an X-ray apparatus mounted to pivot about a vertical axis, cables have been draped from the ceiling to a location on the apparatus. Sometimes the cables have been suspended from the end of a cable boom mounted to the ceiling to pivot about a vertical axis and generally follow the motion of location on the X-ray apparatus where the cables enter the apparatus. Such ceiling mounted systems have required a certain minimum ceiling height in the room where the apparatus is installed. They also add to the bulk and unwieldiness of the entire apparatus.

SUMMARY OF THE INVENTION

The present invention provides a cable handling system for routing at least one cable from a stationary location to a moveable location which overcomes the above problems. A sleeve, which allows the cable to flex and slide, envelopes a length of the cable in an area of the cable where the cable is subject to flexing. Means are provided for holding the sleeve in the area where the cable is flexed. Means, which may be the same as the holding means, are also provided for limiting the movement of the sleeve to a certain space so that flexing of the cable inside the sleeve is limited to said space. This construction manages the flexing and sliding of the cables in a compact space as the structure to which they are routed is moved without draping or providing excess slack in the cables.

In a preferred form, the moveable location to which the cables are routed is rotatable about an axis through a hub, the cable is routed past the hub, and the sleeve is held in the area of the hub. Means are provided adjacent to the hub for restraining the cable longitudinally and allowing limited rotation of the cable about at least one axis substantially parallel to the axis through the hub. As the moveable location is rotated about the hub axis, the sleeve keeps the cables from bunching up, buckling, intertwining and tangling, and allows the cables to flex and slide within it as required to take up the movement of the moveable location. The restraining means also provides for limited angular movement of the cables to adjust the position of the cable to the new angular position of the hub.

Preferably, the sleeve is held in tension. Holding the sleeve in longitudinal tension (along the direction of the cables) helps keep the sleeve in longitudinal position over the cables and keeps it from bunching up around the cables. Holding the sleeve in transverse tension (along the direction perpendicular to the cables) helps hold the sleeve flat in the transverse direction, which is especially useful if the cables or subgroups of the cable are held in side-by-side relationship along the transverse direction. Holding the sleeve in tension in either or both directions also helps keep the cables from bunching up, buckling, intertwining and tangling.

In another aspect, the means for holding the sleeve and the means for limiting the movement of the sleeve include means attached to a stationary location adjacent to the hub and means attached to the moveable location. Attaching the rearward portion of the sleeve to a stationary location where the cables enter the hub helps align the sleeve to the angular position around the hub where the cables enter the hub. Attaching the forward portion to the moveable location helps align the forward portion of the sleeve with the location on the hub where the cables are transversely stationary. Thereby, the sleeve is held between the fixed angular location where the cables enter the hub area and the location at the other side of the hub where the cables are held transversely (i.e., fixed angularly relative to the hub). As the hub is rotated, the sleeve tends to follow the rotation and align the cables between the fixed angular location and where they are fixed angularly relative to the hub.

Where a group of many cables is being routed, the sleeve is preferably divided into two or more longitudinal compartments to divide the group into at least two subgroups. This prevents the cables of each subgroup from interfering with the cables of any other subgroup. The compartments may also be arranged in side-by-side relation to arrange the subgroups in side-by-side relation. Subjecting the sleeve to tension, especially in the transverse direction, helps keep the subgroups in side-by-side relation and also the cables within each subgroup in order. Surfaces sandwiching each subgroup may also be provided to hamper buckling of the cables in the direction of the thickness of the sleeve.

In another aspect, there may be a straight section of cables on the side of the hub opposite from where they enter the hub. In this area, the cables do not flex, but must be able to slide relative to one another to account for differences in longitudinal movement due to different transverse locations of the cables. This movement may subject the cables to tension or to compression, depending upon which way the hub is being rotated. In this straight section, means are therefore provided to give longitudinal support to the cables against buckling under compressive loads. Preferably, rigid partitions divide the group of cables into subgroups for transverse support and top and bottom rigid surfaces enclose the subgroups so they are supported in all directions.

It is therefore a principal object of the invention to provide a cable handling system which allows routing a cable or a group of cables from a stationary location to a moveable location.

It is another object of the invention to provide such a cable handling system which is useable in a compact space.

It is another object of the invention to provide such a cable handling system which does not require draping cables or excess slack in the cables outside of the moveable apparatus to which the cables are connected.

It is another object of the invention to provide a cable handling system which helps prevent bunching up, buckling, tangling and intertwining of the cables.

It is another object of the invention to reduce fatigue on cables routed to a moveable apparatus.

These and other objects of the invention will be apparent from the drawings and from the detailed description.

DESCRIPTION OF THE DRAWINGS

The present invention is described below, as required by 35 U.S.C. §112, in such full detail as to enable those skilled in the art to practice the invention and also to set forth the presently-contemplated best mode for its practice, all by reference to the following drawings in which:

FIG. 3 is a side view of the apparatus shown in FIG. 2 illustrated with a portion broken away;

FIG. 4 is a sectional view taken along the plane of the line 4—4 of FIG. 2;

FIG. 6 is a top plan view of a sleeve for the cable handling system of the present invention;

FIG. 7 is a side elevation view of the sleeve of FIG. 6;

FIG. 8 is a sectional view taken from the plane of the line 8—8 of FIG. 6 and shown with cables drawn in;

FIG. 9 is a detail view in section of a cable rotator portion of the cable handling system disclosed;

FIG. 11 is a sectional view taken along the plane of the line 11—11 of FIG. 9; and FIG. 12 is an end view of the cable holder bar shown in FIG. 11 taken along the plane of the line 12—12 of FIG. 11.

DETAILED DESCRIPTION OF THE PREFERRED EMBODIMENT

Figure 1:
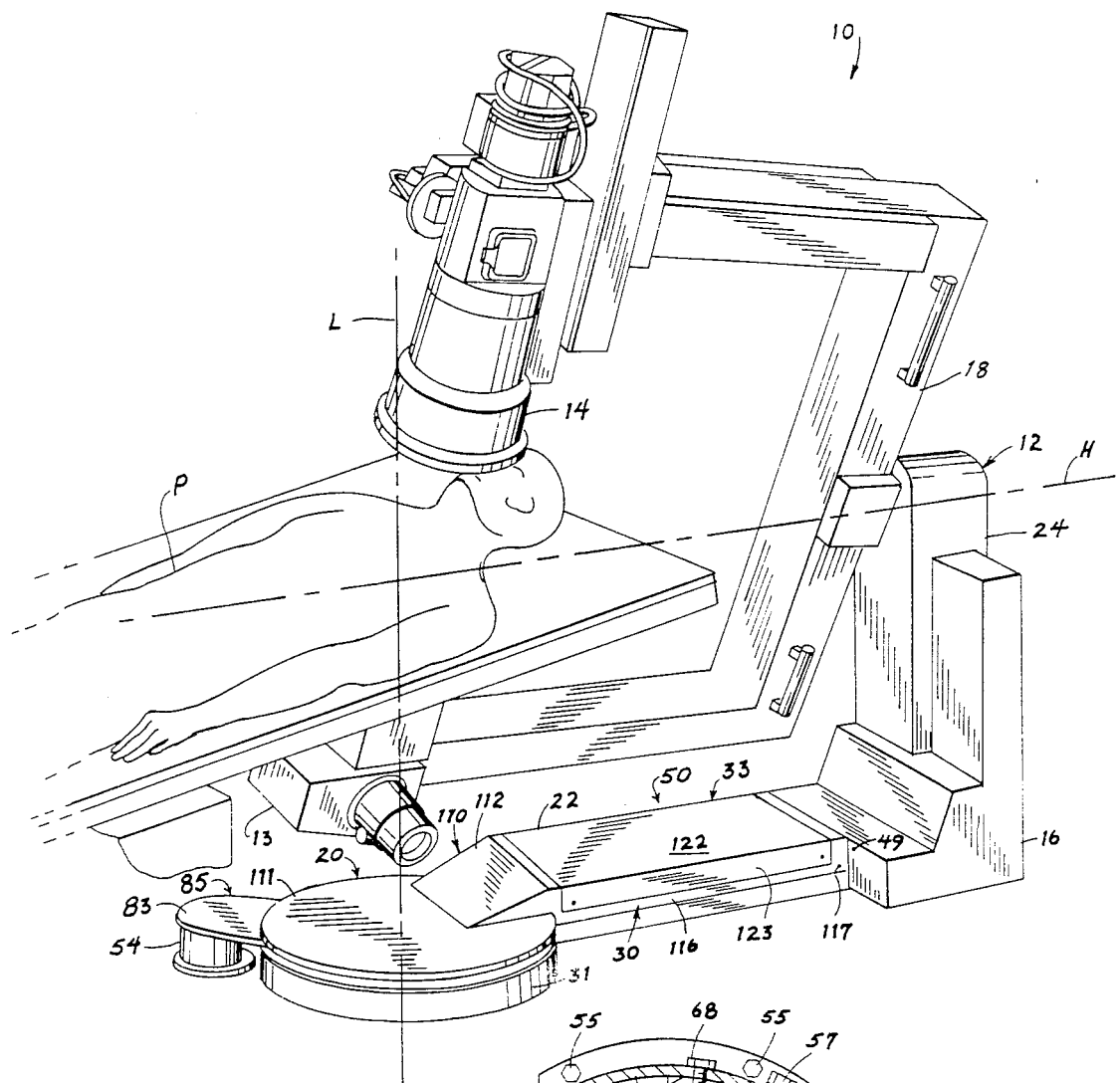
FIG. 1 is a perspective view of an X-ray apparatus incorporating a cable handling system of the present invention.

FIG. 1 illustrates an X-ray apparatus 10 which incorporates a cable handling system of the present invention. The X-ray apparatus 10 generally comprises an L/U support 12, an X-ray source 13 and an X-ray detector 14. X-ray apparatus having these elements are well known and commercially available. The application of a cable handling system of the present invention will be described with reference to such an apparatus, however, the present invention may be applicable to other apparatus which involve routing cables to a moveable location.

The L/U support 12 includes an L-shaped support 16 and a U-shaped support 18. The L-shaped support 16 is made up of serially connected hub 20, horizontal arm 22 and vertical arm 24. The U-shaped element 18 is rotatably connected to the upper end of the vertical arm 24 to rotate about a horizontal axis H. The hub 20 is mounted to the floor to rotate the L-shaped support 16 in a horizontal plane about a vertical axis L which extends through the center of the hub 20 and intersects the horizontal axis H. The rotary motion of the L-shaped support 16 is limited to about 230°, or any other suitable range, as hereinafter described. The L-shaped support 16 may be pivoted through this range in either direction to obtain the correct viewing angle for X-raying the patient P being observed.

Figure 2:
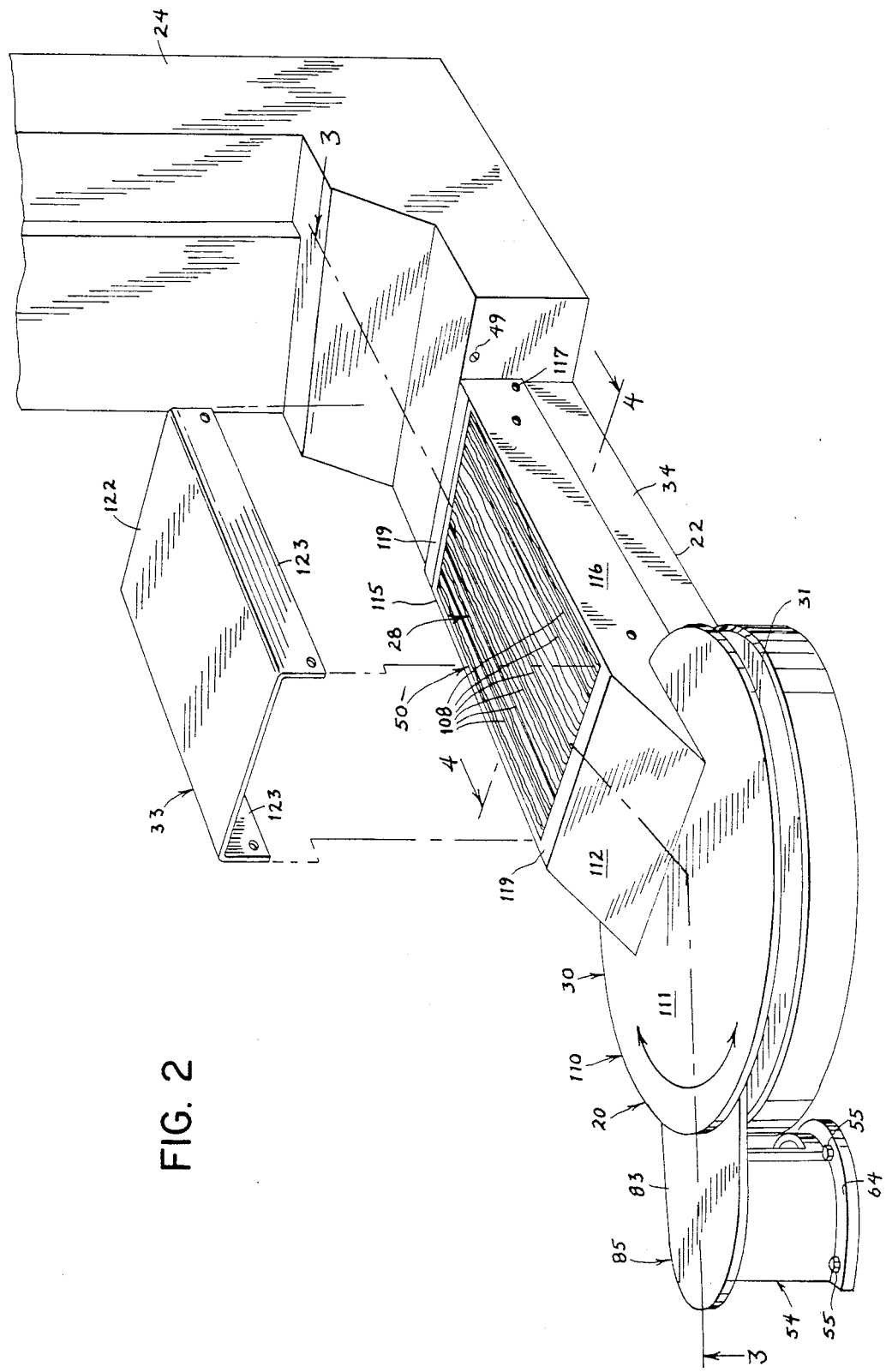
FIG. 2 is a perspective view of the portion of the apparatus of FIG. 1 which incorporates a cable handling system of the present invention shown with a cover removed.

FIGS. 2 and 3 illustrate in more detail the portion of the X-ray apparatus 10 of interest with respect to the present invention. Several electrical cables 28 must be routed to the X-ray apparatus 10 to connect the apparatus 10 to power supplies, controls, and peripheral equipment. Routing of the cables 28 is accomplished in the present invention from a cable trough 26 in the floor, which, of course, is stationary, to the hub 20 and horizontal arm 22, which are moveable. From the arm 22, the cables are routed to the components to which the cables are electrically, optically, or otherwise connected, generally the source 13 and detector 14. Although the cable trough 26 is shown below the surface of the floor, it should be understood that the cables could come from anywhere in the vicinity of the hub 20. Also, the number of cables which must be routed depends upon the particular X-ray apparatus, but generally is less than about 40. As shown in FIG. 4, the cables may range in size from relatively small to relatively large diameter, only being limited by height, space and service requirements.

As the L-shaped support 16 is pivoted about the L axis, the cables 28 must be able to move and flex to accommodate the changed position of the support 16. They must also execute the required movement and flexing largely within a limited space inside the L-shaped support 16. In the area of the hub 20, this space is defined between a first cover 30 and a hub base 31. In the area of the horizontal arm 22, the space is defined by the first cover 30, a second cover 33, and an arm base 34, which is integral with the hub base 31. In this space, the cables 28 are distributed in a group which is substantially rectangular in cross section, with its transverse dimension in the plane of rotation and generally perpendicular to the direction of the cables. The cables 28, which are at the transverse outside of the grouping, such as the cables 36, are subject to more longitudinal movement as the L-shaped support 16 is rotated than the inside cables, such as the cables 35. Hence, if larger cables and smaller cables make up the cable group, it is desirable to arrange the larger cables generally toward the center of the group and the smaller cables toward the outside. However, in some cases, larger cables are more flexible than smaller cables such that they should be distributed toward the outside with the smaller diameter more stiff cables toward the inside.

The cables 28 are usually round in cross section and vary in stiffness. When the L-shaped support 16 is rotated, the cables, because of their different positions and sizes, move relative to one another. Because of their shapes and differences in stiffness and motion, the cables tend to bunch up, overrun one another, intertwine and become tangled when the L-shaped support 16 is rotated. In the absence of a way to restrain the cables against such undesirable behavior, the cables have the potential to flex and also rub excessively on each other and on the walls of the X-ray apparatus enclosing them, which could cause failure in their insulation, deformation of the covers 30 and 33, and fatigue over many cycles which could develop a discontinuity in a conductor (electrical or optical) within the cables.

To limit the cables 28 from bunching up, overrunning one another, intertwining and becoming entangled, a sleeve 38 is provided. The cables 28 run through the sleeve 38 and are enveloped by the sleeve 38 over their length which does the most flexing and is therefore most likely to bunch, overrun, intertwine, entangle and fail due to fatigue and wear. This length is that in the area of the hub 20, and particularly that length in the transverse area through the L axis, which is generally perpendicular to the arm 22.

The sleeve 38 divides the group of cables 28 into subgroups because dividers are sewn into the sleeve 38. Referring to FIGS. 6 and 8, seams 40 run the length of the sleeve 38 to divide the sleeve 38 into seven through-pockets 42A–G. Each pocket 42A–G has a closure 43 which runs its length so that the respective pocket may be completely opened up or closed. After each subgroup of cables 28 is put into its corresponding pocket, closures 43 are closed so that the corresponding pocket envelops the subgroup of cables. The sleeve 38 creates subgroups of cables 28 according to their transverse positions within the entire group. Thus, cables in substantially the same transverse position, which are subjected to substantially the same movements, are grouped together and separated from other subgroups. Although sliding does take place between the cables within each subgroup, the relative motion between the cables of each subgroup is controlled because all of the cables of each subgroup are at similar transverse locations and the maximum difference in motion of all the cables of each subgroup is less than the maximum difference in motion of all the cables of the entire group.

The sleeve 38 also keeps subgroups in position relative to each other. Thus, although some bunching and overrunning may be possible within the cables 28 of each subgroup, it is not possible for the cables in one through-pocket 42A–G to bunch, overrun, intertwine or become entangled with the cables in another through-pocket. It is also not possible for the sleeve 38 to fold over on itself (i.e. with the through-pockets 42A–G overrunning and folding over one another). In addition, each subgroup cannot contort into a larger area than that provided by its through-pocket.

The sleeve 38 is made of a flexible material to conform to the bends and movements of the cables 28. It should also have good wear properties, as it rubs and slides on the first cover 30, the hub base 31 and the cables 28. A suitable material has been found to be nylon mesh and the closures 43 can be any suitable closure, such as a heavy duty plastic zipper. If zippers are used, after they are closed around the cables, a tie wrap 44 can be looped (FIG. 9) through a tang 41 of the zipper and through one of the holes in the nylon mesh of the sleeve 38 to hold the zipper closed.

Means should be provided for holding the sleeve 38 longitudinally in place along the length of the cables 28. In the preferred embodiment, this is accomplished by straps 46 and 47 which extend forward of the sleeve 38 toward the vertical arm 24 and which are sewn into the forward corners of the sleeve. The straps 46 and 47 extend for the length of a straight cable run area 50 and are attached to the sides of the horizontal arm 22 (i.e. to the moveable structure to which the cables 28 are routed) by suitable fasteners 48 and 49, respectively. The straps 46 and 47 may be made of the same nylon mesh material as the sleeve 38 or of any other material cable of subjecting the sleeve 38 to tension.

Straps 52 and 53 are sewn into the rearward corners of the sleeve 38 and extend rearwardly from the sleeve 38 to a cable entry housing 54 which is fixed to the floor by suitable fasteners 55. The rear ends of the straps 52 and 53 are attached to the cable entry housing 54 by fasteners 57 and 58, respectively. In the preferred embodiment, the straps 52 and 53 are extensible and elastic, such as bunge or shock cords. The cable entry housing 54 limits the angular range of motion of the support 16 to about 230°, although the housing 54 could be made larger or smaller to vary the range, suitable stops could be provided, or the size of the arm 22 could be varied.

The straps 52 and 53 and/or the straps 46 and 47 are preferably extensible and elastic to exert a tensile force on the sleeve 38. This allows the sleeve 38 freedom to move with the cables 28 but keeps it from bunching up longitudinally on the cables 28 and also helps keep the entire group of cables 28 and the sleeve 38 flat against the hub base 31.

It is also preferred to have the straps 46, 47, 52 and 53 attached to the four corners of the sleeve 38 and to have them extend away from the corners somewhat diagonally (at an angle toward the outside). This means of anchoring the sleeve 38 helps keep it centered on the hub base 31 and also subjects it to transverse tension which helps hold it flat. However, it is possible that in some applications one strap from each end of the sleeve would suffice or no straps, if the sleeve could be held by other means, such as an attachment to the cables, the hub base 31, or the cover 30, in the hub area.

The cable entry housing 54 covers an opening 56 in the floor where the cables 28 emerge from the cable trough 26. Even if no cable trough 26 is provided, the cables 28 can be made to enter the cable entry housing 54 from the surface of the floor or from other angles. Also, a cover (not shown) may be provided at the rear of the housing 54.

Figure 10:
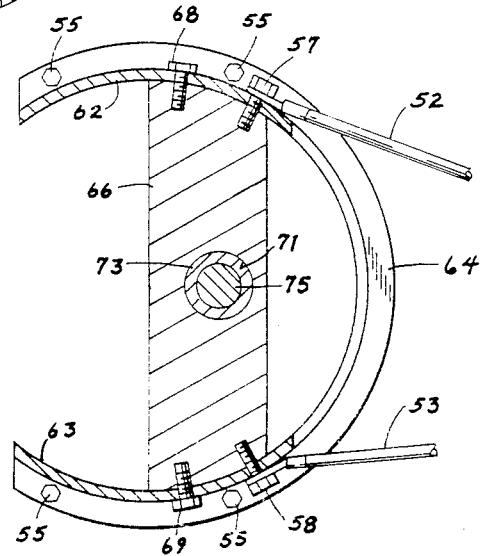
FIG. 10 is a sectional view taken along the plane of the line 10—10 of FIG. 9 of a cable rotator for a cable handling system of FIG. 1.

The cable entry housing 54 is adjacent to the hub 20 and is fixed at an angular position about the hub which is centered on the axis of the arm 22 when the L-shaped support 16 is at the midpoint of its angular range of motion. Referring to FIGS. 9 and 10, the cable entry housing 54 includes two arcuate supports 62 and 63 joined by a mounting flange 64, through which the fasteners 55 extend into the floor. A bar 66 spans the supports 62 and 63 and is secured thereto by the fasteners 57 and 58 and fasteners 68 and 69. The bar 66 has a through-bore 71 into which a bearing 73 is inserted. The bearing 73 journals a post 75 and a snap ring 77 locks the bearing 73 on the post 75. A washer 79 resides between the top end of the bearing 73 and a shoulder of the post 75.

The post 75 is welded to a metal underplate 82 which is secured, such as by a suitable adhesive, to a lubricious overplate 83, which may be made of Delrin or other suitable plastic. The overplate 83, underplate 82 and post 75, which may be generally referred to as a cable rotator 85, can therefore pivot about the vertical axis of the post 75. The overplate 83 should be made of a lubricious material as it may slide on the underside of the cover 30 when the L-shaped support 16 is rotated and/or when the cable rotator 85 pivots. It should be clear, however, that there is no direct connection between the pivoting of the cable rotator 85 and the pivoting of the L-shaped support 16.

The cable rotator 85 also includes a pin 88 having a vertical axis which is welded near the front of the cable rotator 85 and depends downwardly from the underplate 82. The pin 88 extends through the center of and journals a cable holder bar 90 which rests on the hub base 31. The cable holder bar 90 is also made of a lubricious material, such as Delrin plastic, to facilitate sliding on the hub base 31.

Referring to FIG. 11, the cables 28 are divided into four groups in the cable holder bar 90 and are secured to the cable holder bar 90 by tie wraps 92. The tie wraps 92 clamp the cables 28 so that they cannot slide longitudinally relative to one another or relative to the cable holder bar 90 so that they cannot move back into the cable trough 26. A tie wrap (not shown) may also be provided around the cables 28 in the cable trough 26.

The cable holder bar 90 is made in two pieces, with an upper piece 93 having holes 98 therein for the tie wraps 92 to go through, as well as a central hole for the pin 88. A lower piece 94 only has a hole for the pin 88 and holes 97 at the ends thereof, which align with the holes 98 in the ends of the upper piece 93 so that the pieces 93 and 94 can be secured together with tie wraps 99.

Thus, cable holder bar 90 allows pivoting of the cables as a group in the plane of rotation of the hub 20 about the vertical axis of the pin 88, as well as about the vertical axis of the post 75, and restrains the cables 28 longitudinally. There is no direct coupling between the rotary motion of the L-shaped support 16 and the cable rotator 85 and cable holder bar 90. Rather, the motion of the cables as a whole as the L-shaped support 16 is rotated determines the motion of the cable holder bar 90 about the pin 88 and of the cable rotator 85 about the post 75.

The cables 28 begin to become subgrouped by the cable holder bar 90, although there are only four subgroups of them in the cable holder bar 90, as opposed to seven in the sleeve 38. There is a short distance between the cable holder bar 90 and the sleeve 38 which allows the cable holder bar 90 to move without interfering with the sleeve 38. After this short distance of exposed cables, the sleeve 38 begins and extends over a flat or horizontal portion 102 of the hub base 31 and up an inclined portion 103 of the hub base 31 to a crest 104 which is integral and coterminous with the arm base 34. In the preferred embodiment, the sleeve 38 terminates in the area of the crest 104, although the straps 46 and 47 extend forwardly into the cable run area 50.

The sleeve 38 terminates in the area of the crest 104 because from there rearward (toward the cable entry housing 54), the majority of the flexing that the cables are subjected to takes place. However, forward of the sleeve 38, in the cable run area 50 over the arm base 34, in which the cables 28 are substantially straight, the cables do slide relative to one another as the L-shaped support 16 is rotated. Thus, it is still important in the cable run area 50 to provide for movement between the cables 28.

Movement between the cables 28 is provided for in the cable run area 50 by maintaining the subgrouping established by the sleeve 38 throughout the cable run area 50. The subgrouping is maintained by straight partitions 108 (FIG. 4). The partitions 108 maintain the subgroups of the cables 28 to facilitate longitudinal sliding of the cables relative to one another, while holding the cables at a fixed angular position about the hub to enter the cable run area 50. The partitions 108, because they are rigid being made of a material such as metal, also provide longitudinal support to the cables 28 to help keep them from buckling side to side when they are subjected to compression in their movements. The second cover 33 is fixed over the cable run area 50 and cooperates with the arm base 34 to provide longitudinal support to the cables 28 to keep them from buckling vertically, so that the cables cannot buckle in any direction in the cable run area 50.

Figure 5:
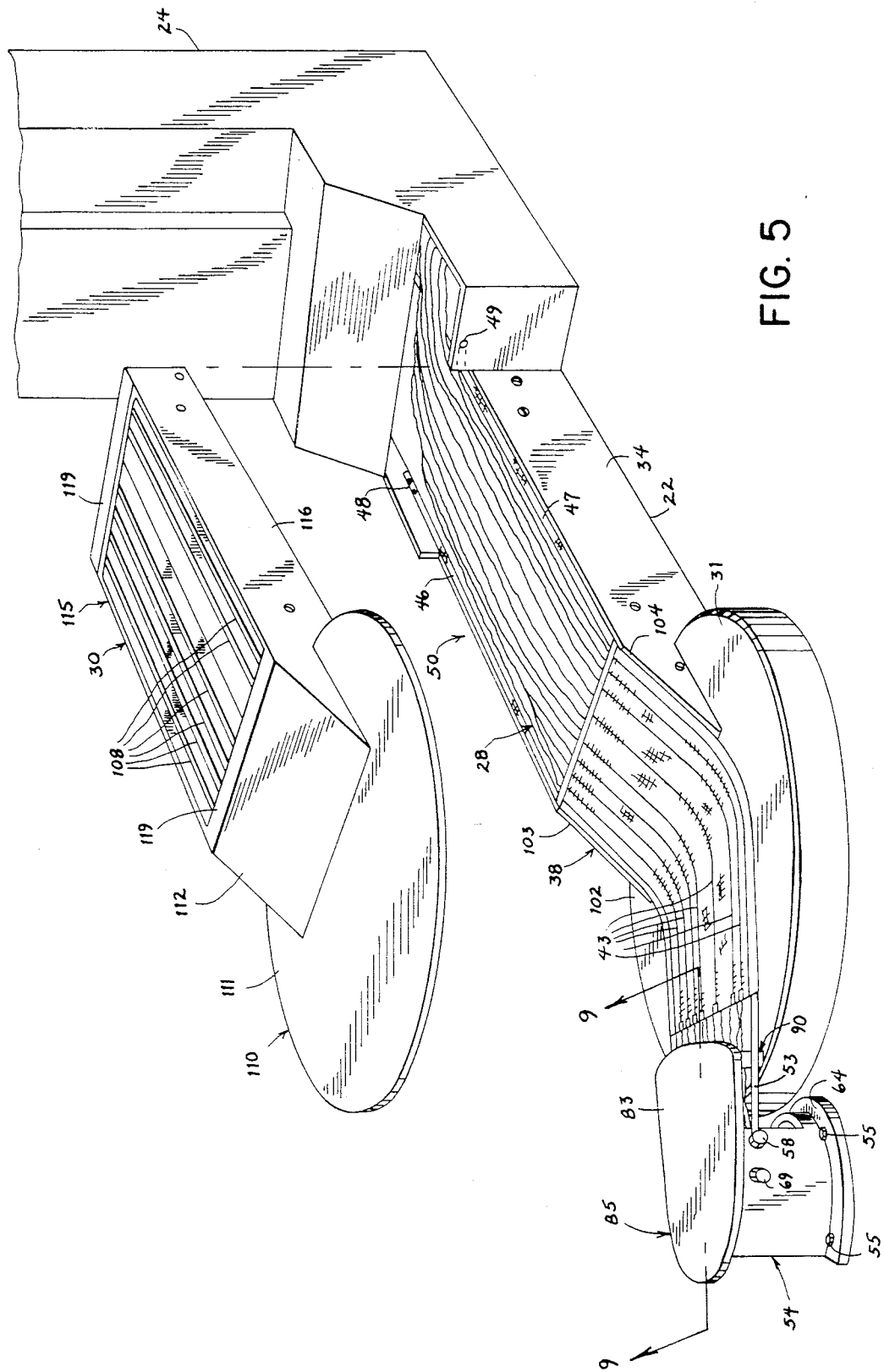
FIG. 5 is a perspective view like that of FIG. 2 but shown with another cover removed.

The partitions 108 start near the forward end of the sleeve 30 (the rearward ends of the partitions 108 may touch the forward end of the sleeve 38) and run forward to the end of the cable run area 50. At the end of the cable run area 50, the cables 28 turn to the side and drape into a space in the X-ray apparatus 10 (FIGS. 3 and 5) where sufficient slack in the cables is provided to allow for movement of the cables as the L-shaped support 16 is rotated. Thereafter, the cables are routed to their destinations in the X-ray apparatus 10. Vinyl or other suitable edge protectors (not shown) should be provided on the ends of the partitions 108 to protect the cables 28 as they rub on the ends, particularly at the forward ends of the partitions.

In the preferred embodiment, the partitions 108 are included as an integral part of the first cover 30. The first cover 30 includes a hub cover 110 which has a substantially flat portion 111 to cover the flat portion 102 of the hub base 31 and also has an inclined portion 112 to cover the inclined portion 103 of the hub base 31. There is only enough clearance between the hub cover 110 and the hub base 31 to sandwich the end of the cable rotator 85, the cable holder bar 90 and the sleeve 38, and to allow the cable rotator 85, cable holder bar 90 and sleeve 38 to move therein. Thus, the subgroups of cables 28 are sandwiched between the hub base 31 and the hub cover 110, with each subgroup adjacent to both the base 31 and cover 110, which helps prevent the cables from buckling vertically as they are subjected to compressive forces as they are flexed. In combination with the straps 46, 47, 52 and 53, the hub base 31 and hub cover 110 limits the movement of the sleeve to a certain space so that flexing of the cables inside the sleeve is also limited to that space.

The hub cover 110 is welded to a cable run portion 115 of the first cover 30. The cable run portion 115 includes sides 116 which are fastened to the arm base 34 with suitable fasteners 117, cross or transverse pieces 119, and the partitions 108, which are welded to the cross pieces 119. The second cover 33 has a top 122 and sides 123 which fit over the sides 116 and are also fastened through the sides 116 to the arm base 34. It is preferred to make the cable run portion 115 and hub cover 110 in one piece to gain additional leverage over the hub cover 110 to hold it down as the cables 28 flex beneath it.

To further facilitate movement of the cables 28, the entire length of the cables throughout the hub 20 and cable run 50 areas can be lubricated, such as with a silicone grease. The sleeve 38 can also be lubricated to aid sliding.

A cable handling system has now been described which allows cable movement, twisting and flexing in a small space without allowing the cables to undesirably bunch up, run over one another, intertwine or become tangled. By so limiting the cable movement, fatigue of the cables is reduced with a correspondingly lower chance for the cable to develop a discontinuity. Also, it is possible to provide for the routing of the cables in a very small area without any moving mechanical parts such as a cable boom. A cable handling system of the present invention also does not impede the motion of the apparatus to which it is connected. Equipment accessibility is also improved because the only possible interference with a user is the relatively unobtrusive cable entry housing 54 mounted on the floor. The overall appearance, arrangement, and packaging of an apparatus including a cable handling system of the invention is also enhanced.

Many modifications and variations of the preferred embodiment will be apparent to those of ordinary skill in the art but will still be within the spirit and scope of the invention. For example, the sleeve 38 need not have seven pockets, but could have any number, and the pockets and cables need not be arranged in a rectangular cross-section. Also, the invention is not limited to use in a horizontal rotational plane or with medical apparatus, but could be used in many different applications where a cable or group of cables must be routed from a stationary location to a moveable location. Therefore, the invention should not be limited by the scope of the preferred embodiment, but only by the claims which follow.

I claim:

1. A cable handling system for routing at least one cable along a cable routing path from a stationary location to a rotatably moveable structure, comprising:
   a hub which is rotatable about a rotational axis, a rotatably moveable structure attached to said hub which is rotatably moveable with said hub;
   a stationary location adjacent to the hub;
   at least one cable routed along a cable routing path from the stationary location past at least a portion of the hub to the rotatably moveable structure;
   a flexible sleeve for sheathing along said cable routing path an articulated length of said cable which is subject to flexing, said sleeve being made of a web of drapable material for sheathing said articulated length of cable and allowing said articulated length of cable to flex and slide within the sleeve;
   means for holding the sleeve under tension between the stationary location and the rotatably moveable structure along the cable routing path; and
   means for restraining the position of the sleeve along said articulated length of cable while allowing said articulated length of cable to slide longitudinally relative to the sleeve;
   wherein the sleeve allows and conforms to limited bending and movements of said articulated length of cable and contains said articulated length of cable between the stationary location and the rotatably moveable structure as the rotatably moveable structure is rotated about the rotational axis.

2. A cable handling system as in claim 1, wherein said stationary location is defined by a stationary structure adjacent to the hub for restraining said cable longitudinally and allowing limited rotation of said cable about at least one axis which is substantially parallel to the rotational axis through the hub.

3. A cable handling system, comprising:
   a moveable structure;
   a stationary location adjacent to the moveable structure;
   a cable routing path from the stationary location to the moveable structure;
   at least one cable running from said stationary location to said moveable structure along said cable routing path, said cable having an articulated length which is subject to flexing along the cable routing path;
   a flexible sleeve for providing a portion of the cable routing path for the articulated length of cable which is subject to flexing, said sleeve being made of a web of drapable material for sheathing said articulated length of cable and allowing said articulated length of cable to flex and slide within the sleeve;
   means for holding the sleeve under tension between the stationary location and the moveable structure along the cable routing path; and
   means for restraining the position of the sleeve along said articulated length of cable while allowing said articulated length of cable to slide longitudinally relative to the sleeve;
   wherein the sleeve allows and conforms to limited bending and movements of said articulated length of cable and contains said articulated length of cable between the stationary location and the moveable structure as the moveable structure is moved; and
   further comprising means for longitudinally opening and closing said sleeve to assemble and remove the articulated length of cable to and from the sleeve.

4. A cable handling system, comprising:
   a moveable structure;
   a stationary location adjacent to the moveable structure;
   a cable routing path from the stationary location to the moveable structure;
   at least one cable running from said stationary location to said moveable structure along said cable routing path, said cable having an articulated length which is subject to flexing along the cable routing path;
   a flexible sleeve for providing a first portion of the cable routing path for the articulated length of cable which is subject to flexing, said sleeve being made of a web of drapable material for sheathing said articulated length of cable and allowing said articulated length of cable to flex and slide within the sleeve;
   means for holding the sleeve under tension between the stationary location and the moveable structure along the cable routing path; and
   means for restraining the position of the sleeve along said articulated length of cable while allowing said articulated length of cable to slide longitudinally relative to the sleeve;
   wherein the sleeve allows and conforms to limited bending and movements of said articulated length of cable and contains said articulated length of cable between the stationary location and the moveable structure as the moveable structure is moved; and
   wherein the sleeve provides said first portion of the cable routing path for multiple articulated lengths of a group of two or more cables and is divided into longitudinal compartments for dividing the group of cables into subgroups.

5. A cable handling system as in claim 4, wherein the sleeve is held in tension transversely.

6. A cable handling system as in claim 4, wherein a second portion of the cable routing path is straight and further comprising means for providing longitudinal support against buckling of the cables in the second portion.

7. A cable handling system as in claim 6, wherein the means for providing longitudinal support against buckling of the cables in the second portion includes rigid partitions for dividing a group of said cables in the second portion into subgroups.

8. A cable handling system as in claim 4, wherein the sleeve is sandwiched between rigid surfaces to prevent bunching up and buckling of the cables within the sleeve between the surfaces.

9. A cable handling system as in claim 4, wherein the moveable structure is rotatable about an axis through a hub and the first portion of the cable routing path provided by the sleeve passes over the hub.

10. A cable handling system as in claim 9, wherein the stationary location is defined by means adjacent to the hub for longitudinally restraining a group of cables passing through the sleeve and allowing limited rotation of the group of cables about an axis substantially parallel to the axis through the hub so that as the moveable structure is rotated about the axis through the hub, the group of cables can rotate about said substantially parallel axis.

11. A cable handling system as in claim 10, wherein the restraining means includes clamping means which is pivoted to a rotator member which is also pivotable relative to the stationary location in the cable routing path at a fixed angular position about the hub.

12. A cable handling system as in claim 9, wherein the longitudinal compartments of the sleeve are in side-by-side relation to one another to hold subgroups of the cable in side by side relation to one another and the sleeve is adapted to be sandwiched between two rigid surfaces with each compartment adjacent to each said surface.

13. A cable handling system, comprising:

a hub having a hub axis, said hub being rotatable about said hub axis;

a stationary structure adjacent to the hub at a fixed angular position about said hub axis;

a group of cables routed along a cable routing path from the stationary structure and past at least a portion of the hub;

means pivotally attached to said stationary structure for clamping said group of cables to allow said group to pivot as the hub is rotated and to hold said group longitudinally and at a fixed angular position about said hub axis;

a flexible sleeve for providing a portion of said cable routing path for said group of cables over the hub, said sleeve being made of a web of drapable material and being subdivided into longitudinal compartments to divide the group of cables into subgroupings for allowing said cables to flex and slide within the sleeve;

means for holding said group of cables at a fixed angular position on the hub, said means being positioned along the cable routing path on the side of the sleeve opposite from the stationary structure and including partitions to maintain the subgroupings of cables delivered by the sleeve; and means for stretching the sleeve between the stationary structure and the means for holding the group of cables at a fixed angular position on the hub to maintain the sleeve in longitudinal tension and to maintain the position of the sleeve over the hub while allowing the cables to slide longitudinally relative to the sleeve.

* * * * *